United States Patent
Hansson et al.

(10) Patent No.: US 6,198,019 B1
(45) Date of Patent: *Mar. 6, 2001

(54) FLEXIBLE ABSORBENT PRODUCT

(75) Inventors: Roy Hansson, Mölndal; Kerstin Johansson, Ulricehamn, both of (SE)

(73) Assignee: SCA Hygiene Products Aktiebolag, Gothenburg (SE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/849,885

(22) PCT Filed: Dec. 22, 1995

(86) PCT No.: PCT/SE95/01577

§ 371 Date: Jun. 17, 1997

§ 102(e) Date: Jun. 17, 1997

(87) PCT Pub. No.: WO96/20669

PCT Pub. Date: Jul. 11, 1996

(30) Foreign Application Priority Data

Dec. 30, 1994 (SE) .................................. 9404522

(51) Int. Cl.⁷ .................................................. A61F 13/15
(52) U.S. Cl. ............. 604/378; 604/385.01; 604/385.03; 604/387
(58) Field of Search .................... 604/368, 369, 604/378–382, 383, 385.1, 385.2, 387

(56) References Cited

U.S. PATENT DOCUMENTS

| | | | |
|---|---|---|---|
| 3,860,003 | * | 1/1975 | Buell .................. 604/385.2 |
| 4,560,372 | * | 12/1985 | Pieniak ................ 604/368 |
| 4,605,402 | * | 8/1986 | Iskra .................. 604/368 |
| 4,631,062 | * | 12/1986 | Lassen et al. .......... 604/378 |
| 4,846,824 | | 7/1989 | Lassen et al. . |
| 4,935,021 | * | 6/1990 | Huffman et al. ........ 604/385.2 |
| 5,053,029 | * | 10/1991 | Yang .................. 604/385.1 |
| 5,171,302 | * | 12/1992 | Buell ................. 604/385.1 |
| 5,300,053 | * | 4/1994 | Genero ................ 604/380 |
| 5,397,316 | * | 3/1995 | La Von et al. ......... 604/378 |
| 5,464,402 | * | 11/1995 | Zajaczkowski ......... 604/378 |
| 5,484,430 | * | 1/1996 | Osborn, III .......... 604/387 |
| 5,514,104 | * | 5/1996 | Cole et al. ........... 604/380 |
| 5,601,544 | * | 2/1997 | Glaug et al. .......... 604/385.2 |
| 5,662,634 | * | 9/1997 | Yamamoto et al. ...... 604/378 |
| 5,713,881 | * | 2/1998 | Rezai et al. .......... 604/382 |

FOREIGN PATENT DOCUMENTS

| | | |
|---|---|---|
| 0 335 252A2 | 10/1989 | (EP) . |
| 0 335 253A1 | 10/1989 | (EP) . |
| 3-123553 * | 5/1991 | (JP) . |
| WO 94/10953 | 5/1994 | (WO) . |
| WO 94/10956 | 5/1994 | (WO) . |

* cited by examiner

Primary Examiner—John G. Weiss
Assistant Examiner—K. M. Reichle
(74) Attorney, Agent, or Firm—Burns, Doane, Swecker & Mathis, L.L.P.

(57) ABSTRACT

An absorbent product such as a sanitary napkin, a diaper, an incontinence pad or similar article, includes an absorbent body having an absorbent layer presenting a first surface and an opposite second surface. A first material layer is arranged in contact with the first surface of the absorbent layer. A second material layer is arranged in contact with the second surface of the absorbent layer. There is at least one bend indication in the form of a through slit or an elongated opening arranged in the absorbent layer. One of the surfaces of the absorbent layer is mutually joined with the material layer in contact therewith, within a region immediately surrounding the bend indication, on both sides thereof. The absorbent layer's opposite surface in this region is not joined to the material layer in contact therewith.

3 Claims, 2 Drawing Sheets

FLEXIBLE ABSORBENT PRODUCT

The present invention concerns an absorbent product such as a sanitary napkin, a diaper, an incontinance pad or a similar item, comprising an absorbent body enclosed betweeen a first liquid-permeable covering layer and a second liquid-impermeable covering layer whereby the absorbent body comprises an absorbent layer having a first and a second surface, and that a first material layer is arranged in contact with the absorbent layer's first surface and that a second material layer is arranged in contact with the absorbent layer's second surface.

BACKGROUND OF THE INVENTION

Lately absorbent products such as sanitary napkins, diapers, incontinence pads or similar items have come to be made thinner and more flexible, while concurrently their component materials have been improved and achieved higher absorbent capacities. Thus products have become both more comfortable and more discrete to wear while their effectiveness has been maintained. Another important advantage is that the products can be packed into less bulky packages whereby storage and transport is appreciably less expensive.

To be able to fully exploit the advantages of the new thinner products, it is however desirable that they have a shape such that no empty, unused regions are formed between products when in a package. Furthermore it is also desirable that before the products are packaged they can be folded together, without loss of shape or function, into a shape which is more managable for the user. From a packaging point of view, such products should be essentially flat and preferably have a rectangular shape.

These requirements, however, correspond badly with the requirements which are placed on the product during use. To achieve a high user comfort and resistance to leakage, the product must in use, take up a three-dimensional form which adopts the user's body shape without chafing or otherwise irritating the user's skin.

Attempts which have been made up to now to solve this problem are most often built upon the use of special shaping elements made of plastic or, or a similar material, which are put in the absorbent body. These shaping elements are activated when the product is used through being subjected to pressure from the user's body, for example by compression between the user's legs. Such shaping elements are described in EP 335,252 and EP 335,253.

The disadvantages with these known shaping elements are many. They are comparatively expensive and complicated to manufacture, which together with the increased material consumption makes the production of the finished product more expensive. With so called disposable products, that is products which are supposed to be discarded after only one use, manufacturing costs and material consumption are both extremely important factors to which considerable attention must be paid both in order that the product can be sold for a reasonable price and also that the quantity of material which has to be transported, stored and finally thrown away should be able to be minimised. Especially from an enviromental view point it is desirable to minimise the quantity of material used.

Another disadvantage is that products containing special shaping elements cannot be packed folded together without the shaping elements being damaged or destroyed. Furthermore, shaping elements bring the risk that sharp folds or corners on the shaping element chafe and irritate the user's skin.

A further method for bringing about the shaping of an absorbent product in use is through providing the product with fold indications in the form of welds or compression lines. The foremost disadvantage with this is that it is impossible to control that the desired bending or folding actually takes place in the intended direction. The risk that the product instead folds or bends in the opposite direction is considerable and thus the leakage resistance of the product is strongly reduced. A further disadvantage is that welds or compression lines are stiff and hard which means that the risk of chafing and irritation of the user's skin is considerable. In particular if the product has been folded together before use there is a big risk that sharp corners or folds have been formed wherever the folding together took place in the direction crossing the fold lines.

BRIEF DESCRIPTION OF THE INVENTION

With the present invention however an absorbent product of the type described above in the introduction is achieved wherein the product set asides problems connected with earlier known such products.

A product formed according to the invention is distinguished principally in that at least one bend indication in the form of a through slit or elongated opening is arranged in the absorbent layer, and in that one of the absorbent layer's surfaces is joined directly to the material layer lying in contact with this surface, within a region which most immediately surrounds the said bend indication and on each side of it, and extends straight across and along essentially an entire length of the at least one bend indication, as well as the absorbent layer's other surface within the said region is not directly joined to the material layer lying in contact with it, whereby bending of the parts of the product which are situated on each side of the bend indication is forced to take place in the direction away from the unjoined surface of the absorbent layer when the product is subjected to compressive forces which are principally directed perpendicular to the bend indication.

Further embodiments and characteristic features will become clear from the subsequent patent claims.

Through arranging in an absorbent layer a slit or elongated opening which extends through the thickness of the layer and the edge parts of which on one side of the absorbent layer are joined to a further material layer which is adjacent to the absorbent layer, while the edge parts of the slit on the opposite surface of the absorbent layer are movable in relation to one another in a direction principally perpendicular to the slit or opening, the bending and shaping of the absorbent body when it is being used can be directed and controlled as desired.

During the use of a product with such an absorbent body the slits interact with the compressive forces which the absorbent body is affected by when it is placed inside a pair of underpants. In this connection the product is subjected to compression between the underpants and the user's body and also to compressive forces from the user's thighs acting principally perpendicular thereto. By the appropriate shaping and positioning of one or more slits or elongated openings, it is possible to cause the absorbent body to shape itself to the user's body during use in such a manner that the risk of leakage of body fluids is minimised while at the same time both user comfort and discretion considerably increase.

In order to function as a distinct, well-defined bend indication, it is important that the elongated opening is not too wide. The opening is therefore most appropriately formed as a slit or as a narrow, slot-shaped hole in the absorbent layer. The width the elongated opening should therefore not be more than 5 mm. In extremely thick absorbent layers (0.5 cm or thicker)it can, however, be necessary to provide openings with a width up to 1.5 cm.)

The improved three-dimensional shaping can be brought about surprisingly enough without any cost increasing and stiffening shaping elements. It furthermore avoids the use of stiffening, difficult to bend and chafing welds, compressions or the like.

BRIEF DESCRIPTION OF THE DRAWINGS

The invention will now be described more closely with reference to the embodiments shown in the enclosed drawings.

DESCRIPTION OF EMBODIMENTS

Figure 1:
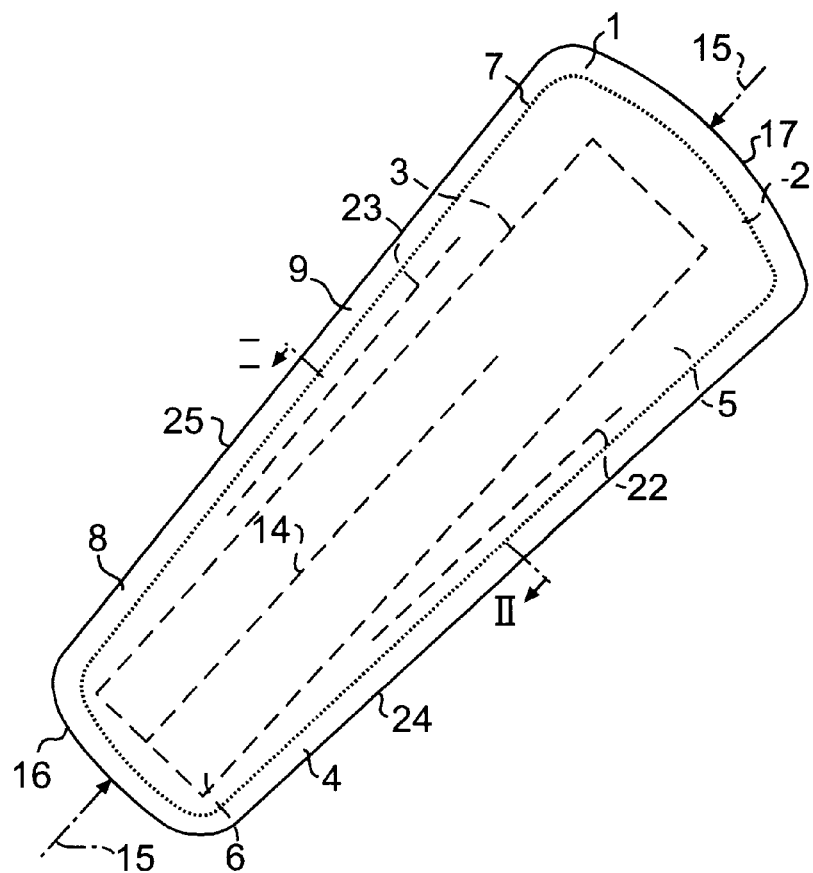
FIG. 1 of the drawings shows a plane view of a sanitary napkin according to the invention seen from the side which is directed towards the user during use.
Figure 2:
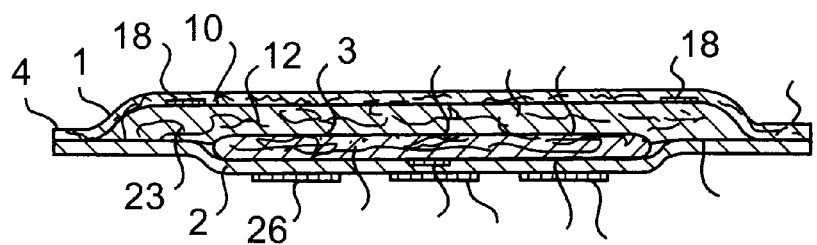
FIG. 2 shows a cross-section along line II—II through the sanitary napkin shown in FIG. 1.

The sanitary napkin show in FIGS. 1–4 comprises a first liquid-permeable covering layer 1, for example a liquid permeable covering layer made of non-woven fabric, woven fabric, perforated plastic film or net applied to the side of a sanitary napkin which is intended to be directed towards the user during use. A second liquid-impermeable covering layer 2, for example a liquid impermeable covering layer made of plastic film or hydrophobic non-woven fabric or woven fabric is applied to the side of a sanitary napkin which is intended to be directed away from the user during use. The two covering layers envelope and are mutually joined around an absorbent body 3 and are mutually connected within parts 4 of the covering layers 1,2 which overhang around the absorbent body 3.

The absorbent body 3 comprises a first absorbent layer 5 arranged immediately inside the liquid-permeable covering layer 1 and appropriately containing a soft, compressible and springy padding of natural or synthetic fibre, or a soft springy foam material. A second absorbent layer 6 is arranged immediately inside the first absorbent layer 5 and appropriately consists of a comparitively stiffer material with high wicking and retention properties and a higher affinity for body fluids than the first absorbent layer 5. A material which fulfills these criteria is described in WO 94/10956. A similar type of material but with properties especially suitable for the absorption of blood is described in WO 94/10953. Conventional compressed layers of fluffed cellulose pulp, absorbent foam material, or different types of tissue laminates are also useable. Absorbent materials with high wicking properties and high liquid retaining properties often have high densities, are comparitively bend-resistant and moderately inelastic. Absorbent layers composed of such material are sensitive to compressive forces since they risk being permanently deformed by the compression force so that sharp folds and fractures are formed in the absorbent material. This often reduces wicking properties through cracks in the absorbent layer which form dispersion barriers.

Another risk is that folds in the absorbent body 3 and covering layers 1,2 serve as wicking channels which lead fluid out of the sanitary napkin with leakage as a consequence. As the first absorbent layer 5 and the covering layers are comparitively soft and yielding they are deformed along with the second absorbent layer 6. The folds which occur in the second absorbent layer 6 therefore also bring about the formation of folds in the rest of the sanitary napkin, even if such folds are not as sharp as those in the stiffer second absorbent layer 6.

The first absorbent layer 5 is intended, when the sanitary napkin is in use, to receive body fluids and transfer them to the second absorbent layer. The fluid is conveyed by capillary action and gravity to the second absorbent layer 6. The material in the first absorbent layer 5 should have a high instantaneous absorption capacity so that all the body fluid emitted can be quickly absorbed in absorbent layer 5 and accomodated there until the fluid has been able to be coveyed to the second absorbent layer 6 which normally has a lower absorbent speed.

Absorbent body 3 can further include so called superabsorbers, or hydrocolloids. Such materials are polymers, usually with a starch or acrylate base, which can absorb and chemically immobilise body fluids in quantities which are equivalent to several times the material's own weight. Superabsorbers are available, for example, in the form of fibres, particles, granules or film. Any type of super-absorber which is suitable can be used. It is possible, for example, to mix in superabsorber in one or both absorbent layers 5,6, composed of wholly or partly of superabsorbent fibres in the form of non-woven fabric or a wadding.

The sanitary napkin has a front part 7, intended in use to be directed towards the front of the user, a rear part 8, intended during use to be directed towards the back of the user, as well as a crotch part 9 between the front part 7 and rear part 8. The sanitary napkin has a essentially elongated trapizoidal shape whereby the front part 7 is a little wider than the rear part 8.

Both of the absorbent layers 5,6 contained in the absorbent body 3 have a first upper surface 10,11, facing the liquid permeable covering layer 1, as well as a second lower surface 12,13, facing the liquid-impermeable covering layer 2. A central slit 14 through the second absorbent layer 6 is arranged along the sanitary napkin's longitudinal centreline 15 and extends along at least part of the length of the sanitary napkin, about three-quarters of the way from the sanitary napkin's rear transverse edge 16 towards the sanitary napkin's front transverse edge 17. The second absorbent layer's 6 lower surface 13 is joined in the region of the central slit 14 to the liquid-impermeable covering layer 2 by glueing or other means. It is essential that the joining region 18 between the two layers 6,2 extends straight across the central slit 14 and along essentially it's whole length. In this way sagging and stretching of the lower surface 13 of the second absorbent layer 6 in the direction perpendicular to the central slit 14 is resisted. This is partly due to the liquid-impermeable layer 2 being less elastic than the absorbent layer 6 and partly because the edges of the central slit 14 are locked in position against one another whereby the central slit cannot expand at the liquid-impermeable layer 2. There is no corresponding joining region on the second absorbent layer's 6 upper surface 11 so the upper surface 11 remains not directly attached and essentially free from direct bonds and whereby the central slit 14 can expand at the surface 11 in a direction which is. Pricipally at right angles to the slit 14.

Figure 3:
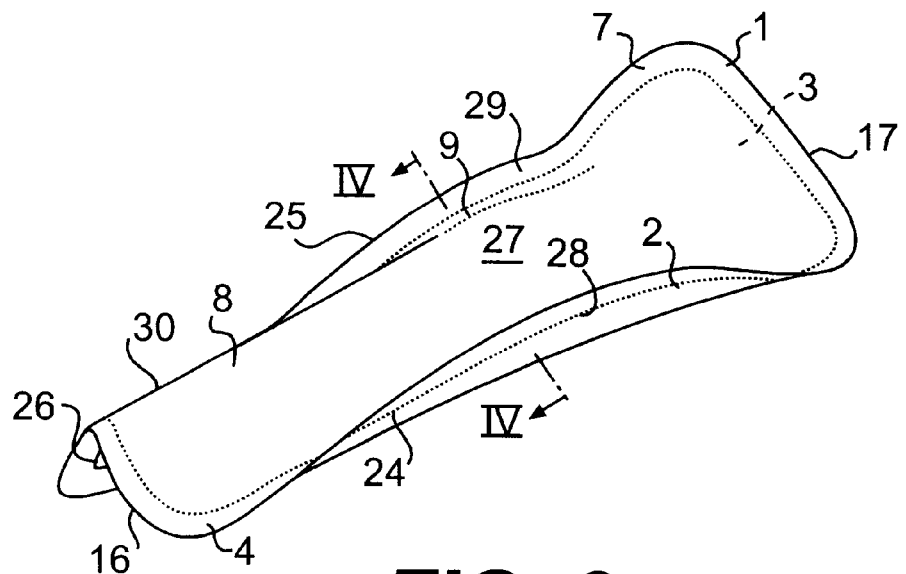
FIG. 3 shows a perspective view of the sanitary napkin of FIG. 1 as it appears during use.
Figure 4:
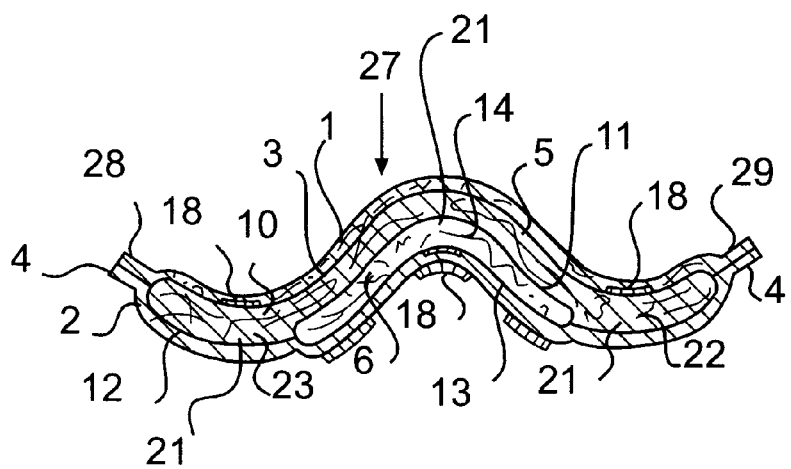
FIG. 4 shows a cross-section along line IV—IV though the sanitary napkin shown in FIG. 3.

The central slit 14 is intended to act as a fold indication and is activated during use when the napkin is compressed between the user's thighs. Through the edges of the central slit 14 being locked in position with respect to one another at the second absorbent layer's 6 lower surface 13 while there is no such locking on the corresponding upper surface 11, compressive forces acting at right angles to the central slit 14 force the sanitary napkin to bend around the slit 14 as shown in FIGS. 3 and 4. In this connection, the central slit is held together by its connection with the liquid-impermeable covering layer 2 which acts as a hinge around which the second absorbent layer 6 can bend. Through this bending, the second absorbent layer's upper surface 11 attains a larger radius of curvature than it's lower surface 13. This means that the upper surface 11 experiences forces which normally should cause stretching and the formation of cracks in the absorbent material. These effects of the bending of the absorbent body are undesirable as they influence the wicking and liquid retention capabilities of the absorbent body in an uncontrolled and usually negative way. The negative effects of bending are avoided in the sanitary napkin shown in FIGS. 1–4 through the edges of the central slit 14 being bent apart at the second absorbent layer's upper surface 11 by the bending which occurs in the upper surface 11. Through the formation of a wedge-shaped groove 21 along the central slit 14 the difference in stretching in the second absorbent layer 6 are evened out to a large degree and in this way it is possible to achieve a controlled, moderately powerful bending of the absorbent body 3 without the appearance of undesired folds or the formation of uncontrolled cracks in the absorbent material.

The first absorbent layer 5 also bends when the second absorbent layer 6 bends about the central slit 14. The bending radius for the first absorbent layer 5 is, however, bigger than the bending radius for the second absorbent layer 6 whereby the tensile forces which occur in the upper surface 10 of the first absorbent layer 5 are less than the tensile forces which cause the central slit 14 to widen at the corresponding surface 11 on the second absorbent layer 6. Through choosing a springy material with a certain degree of elasticity for the first absorbent layer 5, the risk of cracks forming in the first absorbent layer 5 can be completely eliminated. Furthermore, part of the negative effects of the tensile forces on the first absorbent layer 5 are counteracted by it being movable in relation to the liquid-impermeable covering layer 2 and able to slide against it when the absorbent layer 5 stretches during bending.

The first absorbent layer 5 extends over the central slit 14 in the second absorbent layer 6. This means that during use of the sanitary napkin the wedge-shaped groove 21 which forms along the slit 14 when the napkin is bent is completely covered by the soft first absorbent layer 5. By reason of this the surface of the sanitary napkin which is directed towards the user is completely smooth and cannot cause discomfort in the form of chafing or irritation of the user's skin. It is, in general, advisable to arrange a soft, relatively voluminous and unbroken layer over such slits which open towards the user as otherwise the wedge-shaped groove 21 can feel like an irregularity in the sanitary napkins outer layer 1 which is directed towards the user.

A further two through slits 22,23 are arranged in the first absorbent layer 5 along the sanitary napkin's longitudinal edges 24,25 in the crotch part 9. By these edge slits 22,23 the first absorbent layer's 5 upper surface 10 is joined to the liquid-permeable covering layer. As with the joins at the central slit 14, the joining can be made in many different ways, however the essential thing is that the edge slits 22,23 within their respective joining regions 18 are locked so that their edges cannot move apart. At the first absorbent layer's 5 lower surface 12, there is no joining along the edge slits 22,23 to the second absorbent layer's upper surface 11. By arranging the edge slits 22,23 in this way the sanitary napkin will, because of compressive forces arising during use, be forced to bend along the edge slits 22,23 in a direction which is opposite the bending at the central slit 14.

The sanitary napkin in FIGS. 1–4 further comprises a fastening means 26 in the form of longitudinal strings of self-adhesive meltable glue, so-called hotmelt, arranged on the liquid-impermeable covering layer 2. The fastening means 26 is applied to that side of the liquid-impermeable covering layer 2 which is situated on the outside of the sanitary napkin. A removable protective layer (not shown) treated with a release agent, is applied before use over the fastening means 26 to protect it from contamination and undesired sticking before the sanitary napkin shall be used. It is naturally possible to use any other type of fastening arrangement which would be suitable. Examples of such fastening arrangements are surfaces with high friction, hook and loop tape and other types of mechanical fastening means such as straps, push buttons, clips, or similar fastenings.

During use, when the sanitary napkin is squeezed together between the user's thighs, the saniatary napkin adopts the shape shown in FIGS. 3 and 4 with a longitudinal raised portion, so-called hump, and raised side edges 28,29 on both sides of the hump 27. At the crotch part 9 of the sanitary napkin, the height of the hump 27 and the raising of the side edges 28,29 is regulated by the degree of compression between the user's thighs. Through the presence of a certain resistance to bending and a certain bending elasticity in the constituent materials of the sanitary napkin, the sanitary napkin will all the time, in at least some extent, recover its plane shape it if the compression reduces. Futhermore, the soft, springy material in the first absorption layer contributes to holding the hump 27 in contact with the user's body. At the rear part 8 of the sanitary napkin, the napkin is pressed together proportionately powerfully so that in cross-section it adopts the shape of a V with its apex pointed towards the user. This V-shaped ridge 30 carefully follows the user's anatomy in the perineal region and serves as a seal against fluid leakage backwards between the user's buttocks. The raised side edges 28,29 prevent fluid from running out by the longitudinal edges 24,25 of the sanitary napkin. Furthermore the expanded edge slits 22,23 constitute themselves fluid obstructions against side leakage as they obstruct fluid dispersion in the first absortion layer, perpendicular to the edge slits 22,23.

Since the slits 14,22,23 in the absorbent layers 5,6 are arranged as described, the sanitary napkin will during use always take up the desired, predetermined shape. The risk that, for example, the edge parts fold in the opposing direction so that body fluids brought into the sanitary napkin can leak out past the longitudinal side edges 24,25 is nearly completely eliminated.

During use the sanitary napkin is fixed inside the user's pair of briefs by means of the self-adhesive glue in the fastening means 26. In this way the material of the pair of briefs will be shaped with the sanitary napkin and will be bent essentially in the way shown in FIGS. 3 and 4.

It is naturally possible to arrange both the edge slits 22,23 and the central slit 14 in the one and same layer, preferably the second absorbent layer 6. In such an embodiment the two absorbent layers 5,6 must be joined together around the edge slits 22,23. The arrangement is however less preferable as the mutual mobility between the layers 5,6 is then reduced in the region of the central slit 14 as well.

It is further possible to provide the sanitary napkin with only a central slit or only edge slits. It is naturally also possible to imagine placings for the slits other than those described. For example, the central slit can be extended forwards with two divergent slits, where the region around the slits is joined to an adjoining surface on the side of the absorbent layer which is directed towards the liquid-permeable covering layer. In this way, in use, the front part of the sanitary napkin adopts a cupped form which agrees with the user's outer genitals.

A sanitary napkin according to the invention may comprise further layers and components, for example the sanitary napkin can include additional absorbent layers, special wicking layers, or special layers to which slits and openings in the absorbent layer can be joined. Moreover the liquid-permeable covering layer can, in the conventional way, be built up of more than one material layer with mutually different properties.

The invention has been described in the above with reference to a sanitary napkin. Obviously the invention should not be considered as being limited to sanitary napkins but all types of absorbent products which during use shall be transformed from a plane shape to a shape which is adapted to the user's anatomy, can advantageously be provided with slits or elongated openings in accordance with the invention. Moreover, the invention is not limited to the trapezoidal shape described but any shape which is suitable for an absorbent product is, of course conceivable.

The invention consequently should not be interpreted as being limited to the examples described or suggested above, or shown in the drawings, but includes also all modifications thereof or embodiments within the scope of the following patent claims.

What is claimed is:

1. An absorbent product comprising:
   an absorbent body including at least one absorbent layer having opposing surfaces including a first surface and a second surface;
   a first liquid-permeable material layer arranged in contact with the first surface of the absorbent layer;
   a second liquid-impermeable material layer arranged in contact with the second surface of the absorbent layer;
   at least one elongated bend indication opening arranged in said at least one absorbent layer,
   wherein one of said first and second surfaces of the absorbent layer is joined directly with one of said material layers in contact with said one of said surfaces of the absorbent layer within a region immediately surrounding said at least one elongated opening and extending straight across and along essentially an entire length of the at least one elongated opening on each side thereof, and
   wherein the other of said first and second surfaces of the absorbent layer is not directly joined to one of said material layers in contact with said other of said first and second surfaces of the absorbent layer within said region such that, when the product is subjected to compressive forces directed primarily perpendicular to the elongated opening, bending is forced to take place in a direction away from said other of said first and second surfaces of the absorbent layer.

2. An absorbent product comprising:
   an absorbent body enclosed between a first liquid-permeable covering layer and a second liquid-impermeable covering layer, the absorbent body comprising an absorbent layer presenting a first surface and an opposite second surface, the first layer being arranged in contact with the first surface of the absorbent layer and the second layer being arranged in contact with the second surface of the absorbent layer,
   at least one bend indication in the form of a through slit arranged in said absorbent layer,
   one of said first and second surfaces of the absorbent layer is joined directly with the layer in contact with said one surface of said first and second surfaces, within a region immediately surrounding said bend indication, on each side thereof and extending straight across and along essentially an entire length of the at least one bend indication, and
   the other of said first and second surfaces of the absorbent layer is not directly joined to the layer contacting said other of said first and second surfaces in said region, whereby bending of parts of the product which lay on each side of the bend indication, when the product is subjected to compressive forces directed chiefly perpendicular to the bend indication, is forced to take place in a direction away from the other of said first and second surfaces of the absorbent layer which is not joined to the layer contacting said other of said first and second surfaces;
   wherein said through slit has a width of no more than 5 mm.

3. An absorbent product comprising:
   an absorbent body enclosed between a first liquid-permeable covering layer and a second liquid-impermeable covering layer, the absorbent body comprising an absorbent layer presenting a first surface and an opposite second surface, the first layer being arranged in contact with the first surface of the absorbent layer and the second layer being arranged in contact with the second surface of the absorbent layer,
   at least one bend indication in the form of a through slit arranged in said absorbent layer,
   one of said first and second surfaces of the absorbent layer is joined directly with the layer in contact with said one surface of said first and second surfaces, within a region immediately surrounding said bend indication, on each side thereof and extending straight across and along essentially an entire length of the at least one bend indication, and
   the other of said first and second surfaces of the absorbent layer is not directly joined to the layer contacting said other of said first and second surfaces in said region, whereby bending of parts of the product which lay on each side of the bend indication, when the product is subjected to compressive forces directed chiefly perpendicular to the bend indication, is forced to take place in a direction away from the other of said first and second surfaces of the absorbent layer which is not joined to the layer contacting said other of said first and second surfaces;
   wherein said absorbent layer has a thickness of 0.5 cm or greater and said through slit has a width up to 1.5 cm.

* * * * *